United States Patent
Gamwell et al.

(10) Patent No.: US 11,598,703 B2
(45) Date of Patent: Mar. 7, 2023

(54) APPARATUS, SYSTEM AND METHOD FOR MECHANICAL TESTING UNDER CONFINED CONDITIONS

(71) Applicant: Halliburton Energy Services, Inc., Houston, TX (US)

(72) Inventors: Chase Russell Gamwell, Spring, TX (US); Vladimir Nikolayevich Martysevich, Spring, TX (US); Jie Bai, Katy, TX (US); Ronnie Glen Morgan, Waurika, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 353 days.

(21) Appl. No.: 17/046,938

(22) PCT Filed: Jun. 8, 2018

(86) PCT No.: PCT/US2018/036706
§ 371 (c)(1),
(2) Date: Oct. 12, 2020

(87) PCT Pub. No.: WO2019/236105
PCT Pub. Date: Dec. 12, 2019

(65) Prior Publication Data
US 2021/0048381 A1 Feb. 18, 2021

(51) Int. Cl.
*G01N 3/08* (2006.01)
*G01N 3/12* (2006.01)
(Continued)

(52) U.S. Cl.
CPC ............... *G01N 3/10* (2013.01); *G01N 3/02* (2013.01); *G01N 33/24* (2013.01); *G01N 33/38* (2013.01);
(Continued)

(58) Field of Classification Search
CPC ........ E21B 49/005; E21B 49/02; E21B 49/08; E21B 43/267; E21B 49/10; E21B 43/108;
(Continued)

(56) References Cited

U.S. PATENT DOCUMENTS

| 5,226,310 A | 7/1993 | Steiger |
| 6,697,738 B2 | 2/2004 | Ravi et al. |

(Continued)

FOREIGN PATENT DOCUMENTS

| CN | 204855268 U | 12/2015 |
| WO | 2005069014 A1 | 7/2005 |
| WO | 2019236105 A1 | 12/2019 |

OTHER PUBLICATIONS

Jaeger, et al.; "Rock Failure under the Confined Brazilian Test"; Journal of Geophysical Research; vol. 71, No. 10; May 15, 1966; 9 pgs.

*Primary Examiner* — Brandi N Hopkins
(74) *Attorney, Agent, or Firm* — Thomas Rooney; Parker Justiss, P.C.

(57) ABSTRACT

An apparatus for measuring mechanical properties of a downhole material, including first and second fixtures each of the fixtures containing a force application fixture to apply a stress to a specimen of the downhole material. A confining sleeve wraps around portions of the first and second fixtures to form a sealed specimen chamber defined by an inner surface of the confining sleeve and ends of the first and second fixtures nearest the specimen. Wall of a confining chamber contain the first and second fixtures, the confining sleeve and the specimen therein. The confining chamber holds a hydraulic fluid therein such that the hydraulic fluid can exert a confining pressure on the confining sleeve to maintain the seal of the specimen chamber and to maintain contact between the inner surface of the confining sleeve and the specimen when the stress is applied to the specimen.

(Continued)

First channels pass though one or more of the walls of the confining chamber to add and remove the hydraulic fluid to and from the confining chamber. Second channels pass though one or more of the walls of the confining chamber and through one of the first and second fixtures to add and remove a pore space fluid to and from specimen chamber ports open to the specimen chamber to maintain a pore pressure at the specimen chamber ports that is equal to or less than the confining pressure while the stress is applied to the specimen. A system and method are also disclosed.

20 Claims, 6 Drawing Sheets (51) Int. Cl.
G01N 3/10 (2006.01)
G01N 3/02 (2006.01)
G01N 33/24 (2006.01)
G01N 33/38 (2006.01)
(52) U.S. Cl.
CPC ............... G01N 2203/0017 (2013.01); G01N 2203/0019 (2013.01); G01N 2203/0048 (2013.01); G01N 2203/0067 (2013.01); G01N 2203/023 (2013.01); G01N 2203/0226 (2013.01); G01N 2203/0411 (2013.01)
(58) Field of Classification Search
CPC . E21B 17/203; E21B 33/127; G01N 15/0826; G01N 3/10; G01N 33/383; G01N 3/08; C04B 14/06
See application file for complete search history.

(56) References Cited

U.S. PATENT DOCUMENTS

| | | | |
|---|---|---|---|
| 6,922,637 B2 | 7/2005 | Ravi et al. | |
| 7,133,778 B2 | 11/2006 | Ravi et al. | |
| 7,210,343 B2 * | 5/2007 | Shammai | G01N 21/65 |
| | | | 73/152.28 |
| 9,151,154 B2 | 10/2015 | Meadows | |
| 10,197,549 B2 * | 2/2019 | Thomas | E21B 33/14 |
| 2009/0084189 A1 | 4/2009 | McCechan et al. | |
| 2013/0228019 A1 * | 9/2013 | Meadows | G01N 3/08 |
| | | | 73/818 |
| 2015/0027217 A1 | 1/2015 | Kats et al. | |
| 2016/0245061 A1 | 8/2016 | Nguyen et al. | |

* cited by examiner

- 455 — PROVIDE A SPECIMEN OF A DOWNHOLE MATERIAL

- 410 — PLACE A SPECIMEN OF DOWNHOLE MATERIAL BETWEEN FORCE APPLICATION FIXTURES OF FIRST AND SECOND FIXTURES
- 420 — PLACE FIRST AND SECOND FIXTURES, CONFINING SLEEVE AND SPECIMEN INSIDE A CONFINING CHAMBER
- 415 — WRAP A CONFINING SLEEVE AROUND PORTIONS OF FIRST AND SECOND FIXTURES NEAREST TO THE SPECIMEN TO FORM A SEALED SPECIMEN CHAMBER

- 425 — PUMP HYDRAULIC FLUID INTO THE CONFINING CHAMBER TO FILL THE CONFINING CHAMBER WITH THE HYDRAULIC FLUID SUCH THAT THE HYDRAULIC FLUID EXERTS A CONSTANT CONFINING PRESSURE ON THE CONFINING SLEEVE

- 430 — PUMP A PORE SPACE FLUID TO FILL THE SEALED SPECIMEN CHAMBER WITH THE PORE SPACE FLUID INCLUDING PASSING THE PORE SPACE FLUID THROUGH ONE OR MORE SPECIMEN CHAMBER PORTS OPEN TO THE SPECIMEN CHAMBER SUCH THAT THE PORE SPACE FLUID MAINTAINS A CONSTANT PORE PRESSURE AT THE SPECIMEN CHAMBER PORTS THAT IS EQUAL TO OR LESS THAN THE CONFINING PRESSURE

- 435 — APPLY A STRESS TO THE SPECIMEN THROUGH THE FORCE APPLICATION FIXTURES WHILE MAINTAINING THE CONSTANT CONFINING PRESSURE TO MAINTAIN CONTACT BETWEEN THE INNER SURFACE OF THE CONFINING SLEEVE AND THE SPECIMEN AND WHILE MAINTAINING THE CONSTANT PORE PRESSURE, UNTIL MECHANICAL FAILURE OF THE SPECIMEN
  - 440 — PUMPING A SECOND HYDRAULIC FLUID INTO FIXTURE CHAMBERS OF THE FIRST AND SECOND FIXTURES
  - 445 — APPLYING A TENSILE STRESS OR COMPRESSIVE STRESS BY A MECHANICAL FORCE ACTUATOR
  - 450 — APPLY HEAT FROM A HEATING TO MAINTAIN THE HYDRAULIC FLUID AT A CONSTANT TEMPERATURE WHILE THE STRESS IS APPLIED TO THE SPECIMEN

- 460 — PUMP THE HYDRAULIC FLUID OUT OF THE CONFINING CHAMBER

- 465 — PUMP THE PORE SPACE FLUID OUT OF THE SPECIMEN CHAMBER

- 470 — REMOVE THE CONFINING SLEEVE WRAPPED AROUND THE PORTIONS OF THE FIRST AND SECOND FIXTURES

- 475 — REMOVE THE MECHANICALLY FAILED SPECIMEN FROM BETWEEN THE FORCE APPLICATION FIXTURES

APPARATUS, SYSTEM AND METHOD FOR MECHANICAL TESTING UNDER CONFINED CONDITIONS

CROSS-REFERENCE TO RELATED APPLICATION

This application is the National Stage of, and therefore claims the benefit of, International Application No. PCT/US2018/036706 filed on Jun. 8, 2018, entitled "APPARATUS, SYSTEM AND METHOD FOR MECHANICAL TESTING UNDER CONFINED CONDITIONS," which was published in English under International Publication Number WO 2019/236105 on Dec. 12, 2019. The above application is commonly assigned with this National Stage application and is incorporated herein by reference in its entirety.

BACKGROUND

Indirect measurements (such as the Brazilian tensile measurements) are often used to estimate the mechanical properties of downhole materials such a cementitious or core plug specimens. Typically such tests are performed at ambient conditions. Due to the nature of the measurements and specimen geometry it may be impractical to estimate mechanical properties such as the tensile strength or other mechanical properties of a material under conditions experienced in situ. However, with continued advancements of well bore stress simulators, it is becoming more beneficial to have this information. What is needed is an apparatus and method to measure the mechanical properties of downhole materials to give insight into how a material might fail when subjected to confining pressures and temperatures similar to what would be experienced in situ in the wellbore.

BRIEF DESCRIPTION

FIG. 4 presents a flow diagram of selected steps of an example method embodiment of the disclosure the method including the use of any of the apparatus embodiments discussed in the context of FIGS. 1-3.

DETAILED DESCRIPTION

As part of the present invention, we recognized that existing mechanical testing apparatuses and methods may inadequately simulate the in situ subterranean temperature and pressure condition experienced by downhole materials, including cementitious or resin materials used to form the well bore annulus or used as a fracturing fluid, or, the material of underground formations. In contrast, the approach of the present disclosure facilitates the measurement of mechanical properties such as tensile and compression strength under a range of precisely controlled temperatures and pressures that simulate in the subterranean environment of the wellbore and surrounding rock formation. In particular, apparatus embodiments of the disclosure facilitate testing a specimen of the downhole material under temperature-controlled elevated pressure-confining conditions simulative of a subterranean environment. Consequently, the approach of the present disclosure provides a simple and economical way to more precisely assess a mechanical failure envelop of downhole materials as a function of temperature and pressure. In turn, this information allows one to better predict the stability of a cement wellbore casing or to better perform hydraulic fracturing operations by better understanding the stress conditions under which the downhole material mechanically fail, e.g., as part of a fracturing operation.

In the drawings and descriptions to follow, like parts are typically marked throughout the specification and drawings with the same reference numerals, respectively. The drawn figures are not necessarily to scale. Certain features of this disclosure may be shown exaggerated in scale or in somewhat schematic form and some details of conventional elements may not be shown in the interest of clarity and conciseness. Specific embodiments are described in detail and are shown in the drawings, with the understanding that they serve as examples and that they do not limit the disclosure to only the illustrated embodiments. Moreover, it is fully recognized that the different teachings of the embodiments discussed, infra, may be employed separately or in any suitable combination to produce desired results.

Unless otherwise specified, any use of any form of the terms such as "press," "connect," "engage," "couple," "attach," or any other term describing an interaction between elements is not meant to limit the interaction to direct interaction between the elements but include indirect interaction between the elements described, as well. In the following discussion and in the claims, the terms "including" and "comprising" are used in an open-ended fashion, and thus should be interpreted to mean "including, but not limited to." Further, any references to "first," "second," etc. do not specify a preferred order of method or importance, unless otherwise specifically stated but are intended to designate separate elements. The various characteristics mentioned above, as well as other features and characteristics described in more detail below, will be readily apparent to those skilled in the art with the aid of this disclosure upon reading the following detailed description of the embodiments, and by referring to the accompanying drawings.

Figure 1:
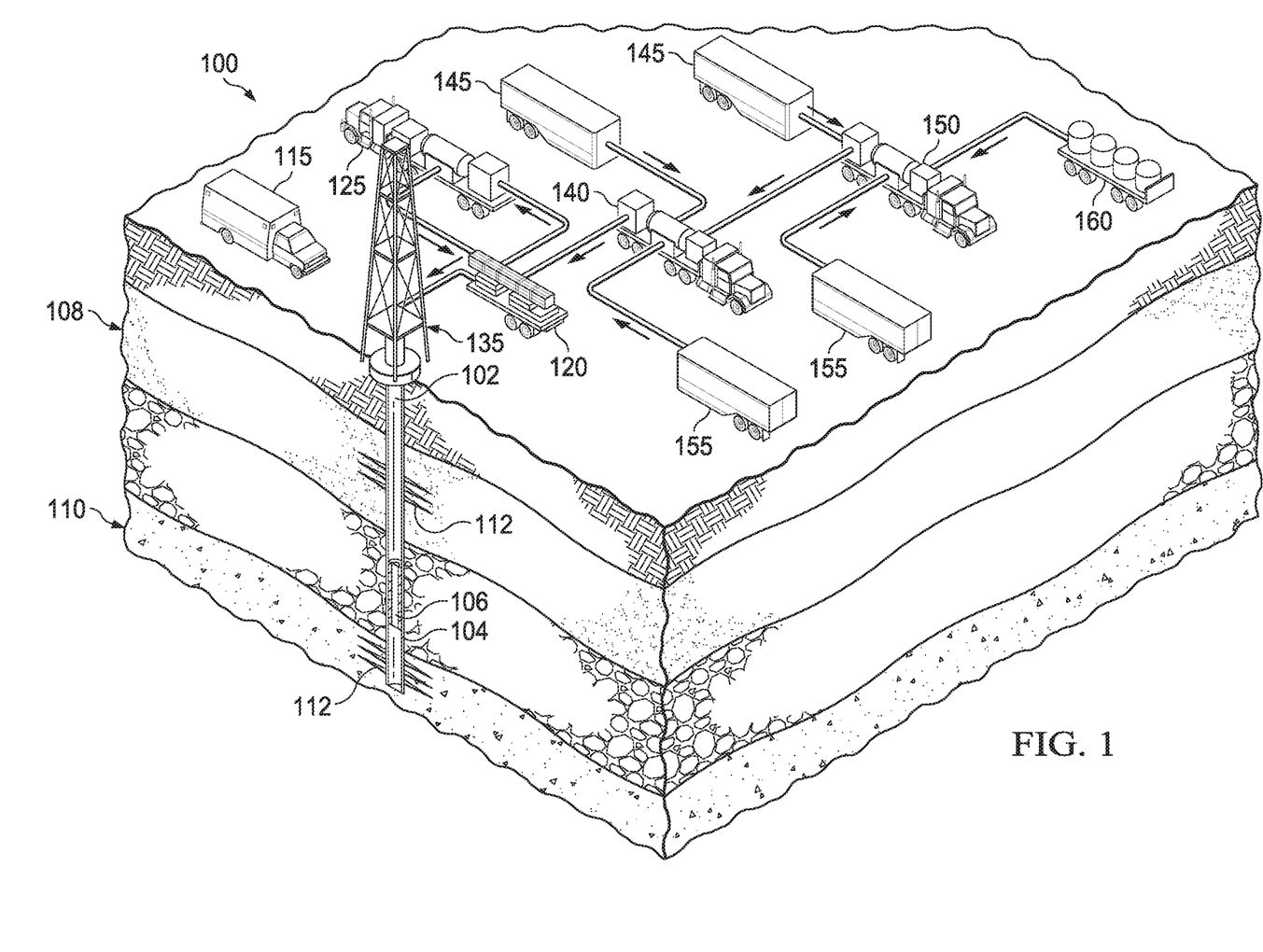
FIG. 1 illustrates a general view of an example hydraulic fracturing system associated with a wellbore for or from which downhole materials can be tested using apparatus, system and method embodiments of the disclosure.

FIG. 1 illustrates a general view of an example hydraulic fracturing system 100 associated with a wellbore 102 for which or from which downhole materials (e.g., cementitious specimens, resin specimens or core plug specimens of a rock formation) can be tested using apparatus, system and method embodiments of the disclosure. The wellbore 102 can include a casing 104 that is cemented or otherwise secured to the wellbore wall. The wellbore 102 can be uncased or include uncased sections. A frac plug tool 106 can be positioned in the wellbore 102 to isolate discrete subterranean formation intervals 108, 110 for different fracture stages that have been identified or reached and a hydraulic fracturing operation may be used to create fractures 112 in the intervals 108, 110 to increase formation porosity for the purpose of increasing oil or gas production. Perforations can be formed in the casing 104 to allow fracturing fluids to flow into formation intervals 108, 110. The fracturing system 100 can include, among other things, an operation control unit 115, a manifold unit 120, a frack pump 125, and a wellhead tree 135 to cap the wellbore 102. The fracturing system 100 can also include a blender system 140 where a cement composition, hydrated gel or other fracturing fluids can be combined with the other fracturing additives or proppants (e.g., sand). The blender system 140 can include one or more of the following: fluid tanks 145, a blender 150, and other fracking component storage tanks 155, such as cement, water, chemical or sand storage tanks. A hydration apparatus 160 can be coupled to the slurry blender system 140.

One skilled in the pertinent art would understand how fracturing fluid, pumped into the wellbore 102 at a high rate to increase the pressure in the wellbore 102, could be used as part of the system 100 to create or increase fractures 112 in the formation intervals 108, 110. For instance, the fracturing fluid, including a cement composition or a hydrated gel, and/or resins (e.g., epoxy or other polymer resins) or composites thereof, can be pumped alone or as a mixture with proppants (e.g., sand or other proppants) or rock formation material into the fractures 112 to prop the fractures in the formation open, to thereby, effectively increase the formation's porosity.

Figure 2A:
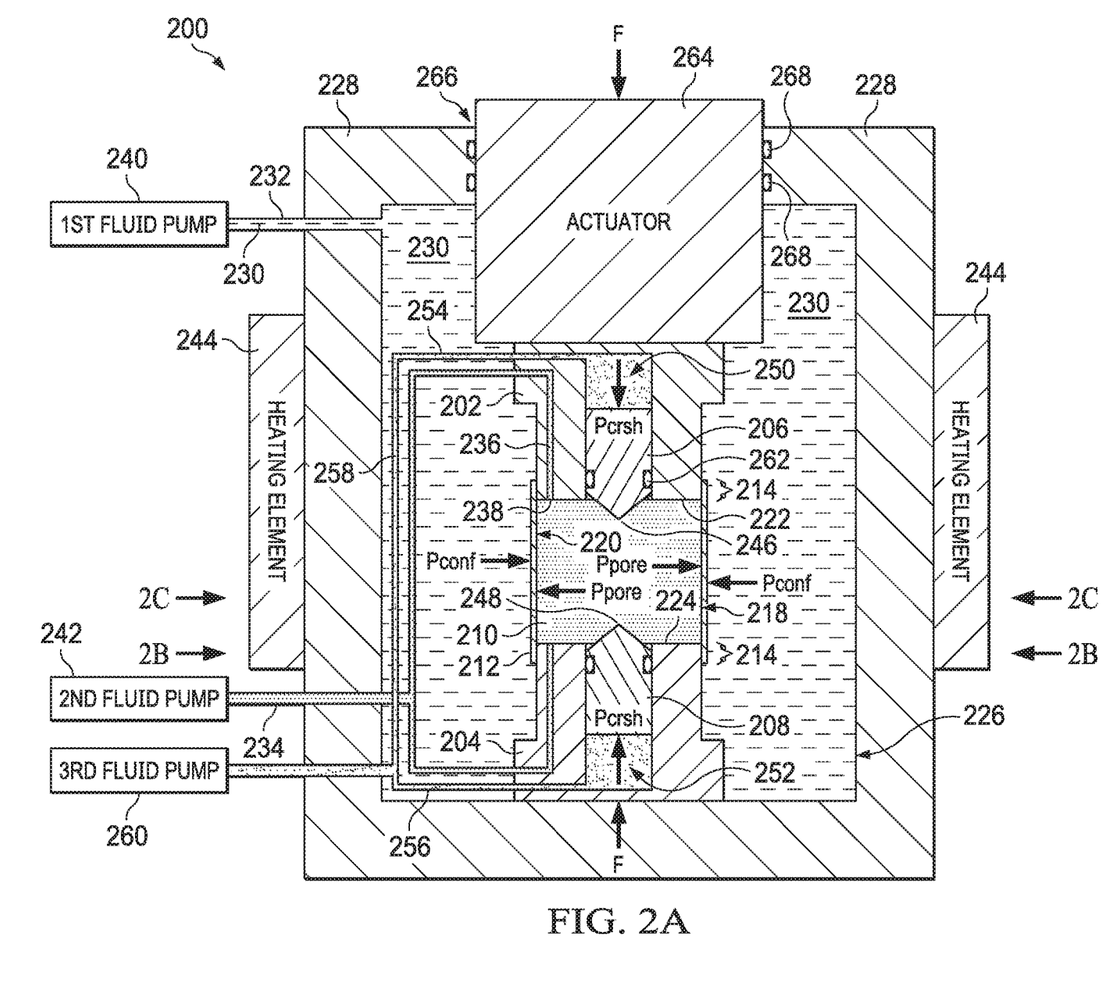
FIG. 2A presents a cross-sectional side view of an example apparatus embodiment of the disclosure.
Figure 2B:
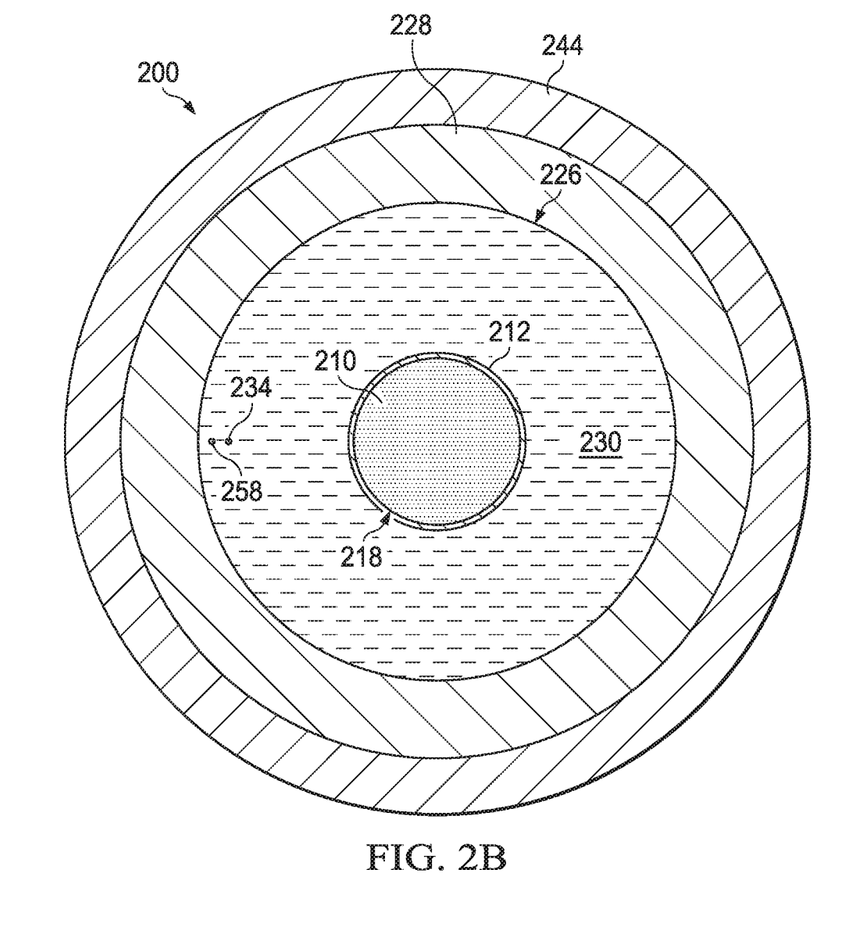
FIG. 2B presents a cross-sectional plan view of the example apparatus shown in FIG. 2A along view line B-B.
Figure 2C:
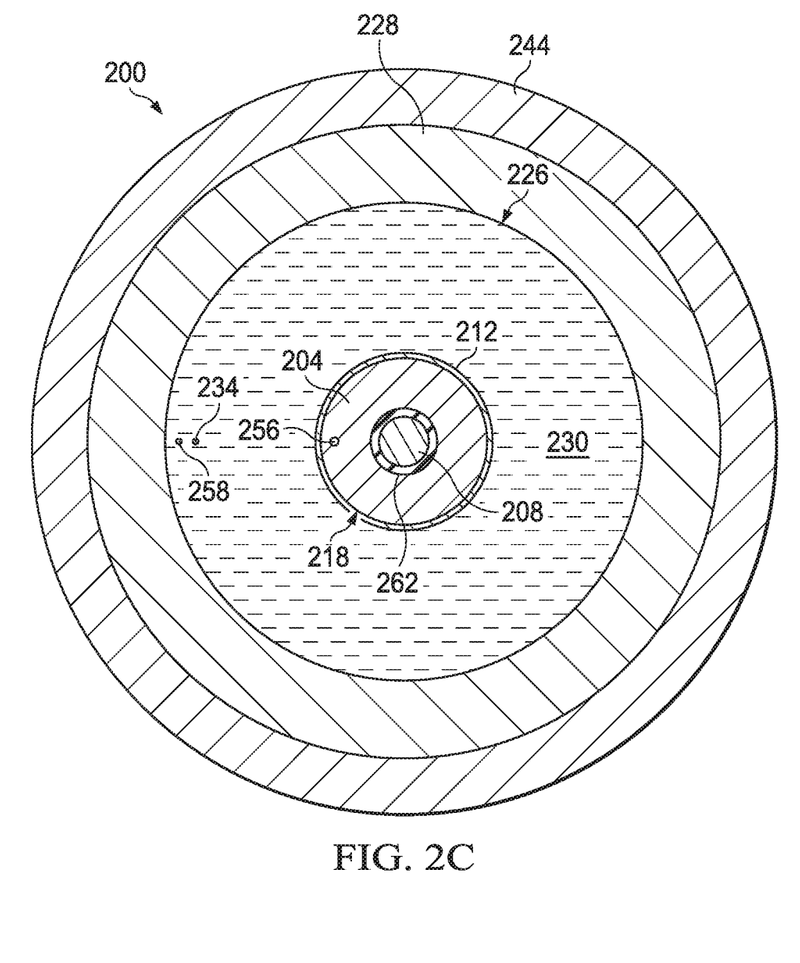
FIG. 2C presents a cross-sectional plan view of the example apparatus shown in FIG. 1A along view line C-C.

One embodiment of the disclosure is an apparatus for measuring mechanical properties of a downhole material. FIGS. 2A, 2B and 2C present a cross-sectional side view, a plan view along view line B, and another plan view along view line C, respectively, of an example apparatus 200 embodiment of the disclosure.

With continuing reference to FIGS. 2A-1C throughout, embodiments of the apparatus 200 can comprise first and second fixtures 202, 204 each of the fixtures containing a force application fixture (e.g., first and second force application fixtures 206, 208, respectively). The force application fixture (e.g., each one of fixtures 206, 208) is configured to apply a stress to a specimen 210 of the downhole material when the specimen 210 is located in-between the first and second fixtures 202, 204. The apparatus 200 can comprise a confining sleeve 212 configured to wrap around portions of the first and second fixtures 202, 204 that are nearest to the specimen 210 (e.g., fixture portions 214 and 216, respectively). The confining sleeve 212 wrapped around the fixture portions 214 and 216 forms a sealed specimen chamber 218, the sealed specimen chamber dimensions are defined by an inner surface 220 of the confining sleeve 212 and ends 222, 224 of the first and second fixtures 202, 204 nearest the specimen 210. The apparatus 200 can comprise a confining chamber 226 having walls 228 configured to contain the first and second fixtures 202, 204, the confining sleeve 212 and the specimen 210 therein. The confining chamber 226 is configured to hold a hydraulic fluid 230 (e.g., hydraulic oil or similar oil) therein such that the hydraulic fluid 230 can exert a confining pressure (Pconf) on the confining sleeve 212 to maintain the seal of the specimen chamber 218 and to maintain contact between the inner surface 220 of the confining sleeve 212 and the specimen 210 when the stress is applied to the specimen 210. The apparatus 200 can comprise one or more first channels 232 (e.g., metal or plastic tubes) passing though one or more of the walls 228 of the confining chamber 226, the one or more first channels 232 configured to add and remove the hydraulic fluid 230 to and from the confining chamber 226. The apparatus 200 can comprise one or more second channels 234 passing though one or more of the walls 228 of the confining chamber 226 and through one of the first and second fixtures 202, 204. The one or more second channels 234 can be configured to add and remove a pore space fluid 236 to and from specimen chamber ports 238 open to the specimen chamber 218. The pore space fluid 236 is configured (e.g., added or removed) to maintain a pore pressure (Ppore) at the specimen chamber ports 238 that is equal to or less than the confining pressure (e.g., Ppore≤Pconf) while the stress is applied to the specimen 210.

In some embodiments, as illustrated in FIG. 2A, the first fixture 202 can be an upper fixture and the second fixture 204 can be a lower fixture (e.g., located below the upper fixture). However in other geometric orientations of the apparatus 200, the first and second fixture could be at a same height (e.g., when the apparatus 200 is tilted 90 degrees relative to the orientation show in FIG. 2A), or the first fixture 202 can be a lower fixture and second fixture 204 can be an upper fixture (e.g., when the apparatus 200 is inverted 180 degrees relative to the orientation show in FIG. 2A).

The term sealed specimen chamber 218 as used herein means that there is substantially no exchange of the hydraulic fluid 230 located in the confining chamber 226 with the pore space fluid 236 located in the specimen chamber 218. One skilled in the pertinent art would understand how to select a composition (e.g., rubber, plastic or other flexible material) of the confining sleeve 218 to have sufficient flexibility to be wrapped around the fixture portions 214 and 216 and sufficient elastic strength to maintain a barrier to prevent exchange between the hydraulic fluid 230 and the pore space fluid 236 while the stress is being applied. Additionally, having a pressure differential between the confining chamber 226 and the specimen chamber 218 (e.g., Ppore<Pconf) may desirably help maintain the barrier. Based upon the present disclosure one skilled in the pertinent art would understand that the selection of the pressure differential to maintain would be a balance depending upon on the elastic strength of the sleeve material and the desire to simulate the downhole environment as accurately as possible.

As illustrated in FIGS. 2A and 2C, the specimen 210 can occupy substantially the entire volume dimension of the sealed specimen chamber 218, but, for porous specimens 210 (e.g., cement or rock specimens) the pore space fluid 236 will also be located in the sealed specimen chamber 218 at least within the pores of the specimens 210.

Maintaining an elevated pore pressure at equal to, or near but less than, the confining pressure may facilitate better modeling of the underground environment of the specimen to correspond more closely to the in situ environment experiences by a downhole cement or rock formation material. For instance, cement and rock materials are porous media and have permeability with respect to fluids present in the downhole environment. Pumping pore space fluid 236 into the specimen chamber 218 and maintaining the pore pressure at or slightly less than the confining pressure facilitates more realistic modeling of such a downhole environment, during the application of the stress. In some testing embodiments, the pore space fluid 236 can be, or include, a formation fluid, a completion fluid or other fluids such as brine, water or gases such as air or methane or other fluids intended to model the down hole environment. For example, in some testing embodiments, the pore pressure can be maintained at a pressure value that is equal to or within less than about 100 psi or about 300 psi of the confining pressure. For example, in some embodiments, the pore pressure can maintained at a pressure value equal to or within less about 1%, or about 2%, or about 10%, of the confining pressure. However, in other testing embodiments, the pore space fluid 236 can be allowed to drain out of the specimen chamber 218 such that the pore pressure can equal about atmospheric pressure.

Consider, as an example, a hydraulic fracturing system 100 such as depicted in FIG. 1, where it is desired to measure the mechanical properties of downhole materials under conditions simulative of the in situ conditions corresponding to two different formation intervals 108, 110 equal to about 5000 and about 10000 feet below the ground surface, respectively. Assuming a hydrostatic gradient in the well bore uniformly increasing at about 1 psi/ft, the overburden pressure at the two formation intervals 108, 110 would equal about 5000 psi and about 10000 psi, respectively. To perform mechanical stress testing simulative of such environments, during the application of the stress using the apparatus 200, the confining pressure could be maintained at about 5000 psi and 10000 psi, respectively, and the pore pressure could be maintained at about 5000 or about 4700 to 4900 psi, and, about 10000 psi, or about 9700 to about 9900 psi, respectively. In some mechanical stress tests using the apparatus 200, during the application of the stress, the confining pressure could be maintained at about 5000 and 10000 psi, respectively, and the pore pressure could be maintained at about 5000 or about 50, 100 or 500 psi lower than 5000 to 4900 psi, and, about 10000 psi, or about 100, 200 or 1000 psi lower than 10000 psi, respectively. In still other mechanical stress tests using the apparatus 200, during the application of the stress, the confining pressure could be maintained at about 5000 and 10000 psi, respectively, and the pore pressure could be equal about atmospheric pressure (e.g., about 14.7 psi).

As further illustrated in FIG. 2A, in some embodiments, the first channels 232 can be connected to a first pump 240. The first pump 240 can be configured to maintain the confining pressure constant (e.g., a target confining pressure value within ±0.1 or ±1 percent, in some embodiments) while the stress is applied to the specimen 210. In some embodiments, the second channels 234 can be connected to a second pump 242, the second pump 242 and configured to maintain the pore pressure constant (e.g., a target pore pressure value within ±0.1 or ±1 percent, in some embodiments) while the stress is applied to the specimen 210.

As further illustrated in FIG. 2A, in some embodiments, the apparatus 200 can further include a heating element 244 configured to maintain the hydraulic fluid 230 at a constant temperature while the stress is applied to the specimen 210. For example, the heating element 244 can be or include heating tape or a water-circulating jacket in contact with the confining chamber walls 228 so as to facilitate heat transfer to or from the hydraulic fluid 230 filled confining chamber 226 in order to adjust the specimen chamber 218 and the specimen 210 to a temperature equal to a value that simulates the downhole environment. For instance, continuing with the above example, and assuming an increasing uniform temperature gradient of about 15° F. per 1000 ft of depth and a surface temperature of 70° F., the temperature at the two formation intervals 108, 110 at depths of 5000 ft and 1000 ft would equal about 145° F. and about 220° F., respectively. In some such embodiments, during the application of the stress, the temperature of the hydraulic fluid 230 could be maintained constant at about 145° F.±1° F. and about 250° F.±1° F., respectively.

One skilled in the pertinent art would understand how the stress applied to the specimen could be a compressive or tensile stress depending upon the directions of forces (e.g., F, FIG. 2A) applied to the specimen 210, e.g., through the force application fixtures 206, 208 and depending upon the shape of the part of the fixtures 206, 208 contacting the specimen.

As further illustrated in FIG. 2A, for some embodiments of the apparatus 200, an end of each of the force application fixtures 206, 208 (e.g., ends 246, 248, respectively) nearest the specimen 210 can be or include wedge-shaped or protruding point-shaped crush fixtures, to apply forces so as to create tensile stress inside the specimen, e.g., to facilitate performing indirect tensile strength testing of the specimen 210. In other embodiments the ends 246, 248 can have a flat surface to apply forces so as to create compression stress inside the specimen e.g., to facilitate performing compression strength testing of the specimen 210. Based on the present disclosure one skilled in the pertinent art would appreciate how other differently shaped force application fixtures 206, 208 ends 246, 248 could be implemented in the apparatus 200 to facilitate performing of these or other mechanical tests on the specimen 210.

As further illustrated in FIG. 2A, in some embodiments of the apparatus 200, the first and second fixtures 202, 204 can each include a fixture chamber 250, 252. At least a portion of each one of the force application fixtures 206, 208 can be located in the respective fixture chamber 250, 252 of the first or second fixture 202, 204. Each of the fixture chambers can be connected to one or more third channels 254, 256 configured to add or remove a second hydraulic fluid 258 (e.g., a hydraulic oils or similar oils) to and from the one fixture chamber 254, 256. The fixture chambers 250 can be configured to hold the second hydraulic fluid 258 therein such that the second hydraulic fluid 258 can apply a crushing pressure (Pcrsh) to the force application fixtures 206, 208 as part of applying at least a portion of the stress, as a compressive stress, to the specimen 210.

For instance, as part of applying the stress, the force application fixtures 206, 208 can apply opposing compressive forces, that is, each of the compressive forces applied from the force application fixtures 206, 208 are configured to move in opposing directions (F, FIG. 2A) to each other towards the specimen 210. To apply a compressive force to the specimen the crushing pressure is greater than the pore pressure (Pcruch>Ppore). As non-limiting examples, the crushing pressure may be about 10, 30, 100, 300, 1000, 3000, . . . psi greater than the pore pressure. Based on the present disclosure, one skilled in the pertinent art would understand how to adjust the crushing pressure to provide a suitable range of compressive forces to cause stress-induced mechanical failure of the specimen. For instance, the crushing pressure may be increased at a steadily increasing rate (e.g., about 1, 10, or 1000 psi/s) as part of applying a target stress rate to the specimen in accordance to a standardized mechanical failure testing protocol. One skilled in the pertinent art would understand how the amount and rate of applied crush pressure applied could be adjusted depending on factors such as the shape and physical property of the specimen (e.g., hard versus brittle material), the shape of the ends 246, 248 of the force application fixtures 206, 208 that contacts the specimen (e.g., pointed versus wedge shaped applicator tips) as well as the temperature and confining pressure that the specimen is maintained at.

Providing first and second fixtures 202, 204 with such fixture chambers 250, 252 can advantageously provide an apparatus 200 that is readily compatible with an existing load frame system for measuring mechanical properties. For instance, the self-contained apparatus 200 can be coupled into or on a load frame mechanical testing system with no or with little modification of the system in order to apply stress to the specimen 210.

As further illustrated in FIG. 2A, in some embodiments of the apparatus 200, to facilitate controlling the application of the crushing pressure, each of the one or more third channels 254, 256 can be connected to a third pump 260. The third channels 254, 256 can pass through one or more of the walls 228 of the confining chamber 226 and through one of the first and second fixtures 102 to the respective fixture chamber 250, 252. The third pump 260 can be configured to apply adjustable amounts of the crushing pressure as part of applying the compressive stress to the specimen 210 until compression failure of the specimen 210.

As further illustrated in FIGS. 2A and 2B, in some embodiments of the apparatus 200, to facilitate maintaining a fluid seal between the specimen chamber 218 and fixture chambers 250, 252 (e.g., substantially no exchange between the second hydraulic fluid 258 in the fixture chambers 250, 252 and the pore space fluid 236 in the specimen chamber 218) the first and second fixtures 202, 204 can further include one or more gaskets 262 (e.g., O-rings made of rubber, plastic or other sealing material). The one or more gaskets 262 can be located between the fixture chamber and the force application fixture in the fixture chamber (e.g., between chamber 250 and force application fixtures 206, and, between chamber 252 and force application fixtures 208) to help prevent exchange of the second hydraulic fluid 258 and the pore space fluid 236.

As further illustrated in FIG. 2A, in some embodiments, to provide an alternative or additional means of applying the stress, the apparatus 200 can further include a mechanical force actuator 264. Embodiments of the actuator 264 can be configured to pass through one or more openings 266 in one or more of the walls 228 of the confining chamber 226 to connect to one of the first or second fixtures (e.g., first fixture 202 or second fixture 204). In some embodiments, a second actuator 264 can pass through one or more of the walls 228 to connect to the other one of the first or second fixtures (e.g., the other of second fixture 204 or first fixture 202). The actuator 264 can be configured to apply at least a portion of the stress through the one or both of first fixture or second fixtures 202, 204 to the specimen 210 as a compressive stress or a tensile stress until mechanical failure of the specimen 210.

In some embodiments of the apparatus 200, the stress can be applied as a combination or sequence of compressive or tensile stresses from stresses applied through both the force application fixtures 206, 208 via crushing pressure and via the actuator 264, or, the stress can be applied by only one of these mechanisms.

As further illustrated in FIG. 2A, in some embodiments, to facilitate maintaining a fluid seal between the confining chamber 226 and the environment outside of the apparatus 200 the apparatus 200 can further include including one or more second gaskets 268 (e.g., O-rings made of rubber, plastic or other sealing material). The gaskets 268 can be located between the one or more openings 266 in the confining walls 228 and the actuator 264 and configured to help prevent an escape of the hydraulic fluid 230 from the confining chamber 228.

Some embodiments of the specimen 210 of the downhole material can include one of: a cementitious or resin materials for use to form a wellbore downhole annulus, cementitious material for use as a fracturing material, resins (e.g., epoxies) or composites of resins and proponent for use fracturing material materials, or, a core plug of a downhole rock formation.

In some embodiments, the hydraulic fluid can include hydraulic oil and the pore space fluid includes one of: formation fluid, completion fluid, brine, water of gas. In some such embodiments the second hydraulic fluid 258 can have the same or a different composition as the hydraulic fluid 230.

Figure 3:
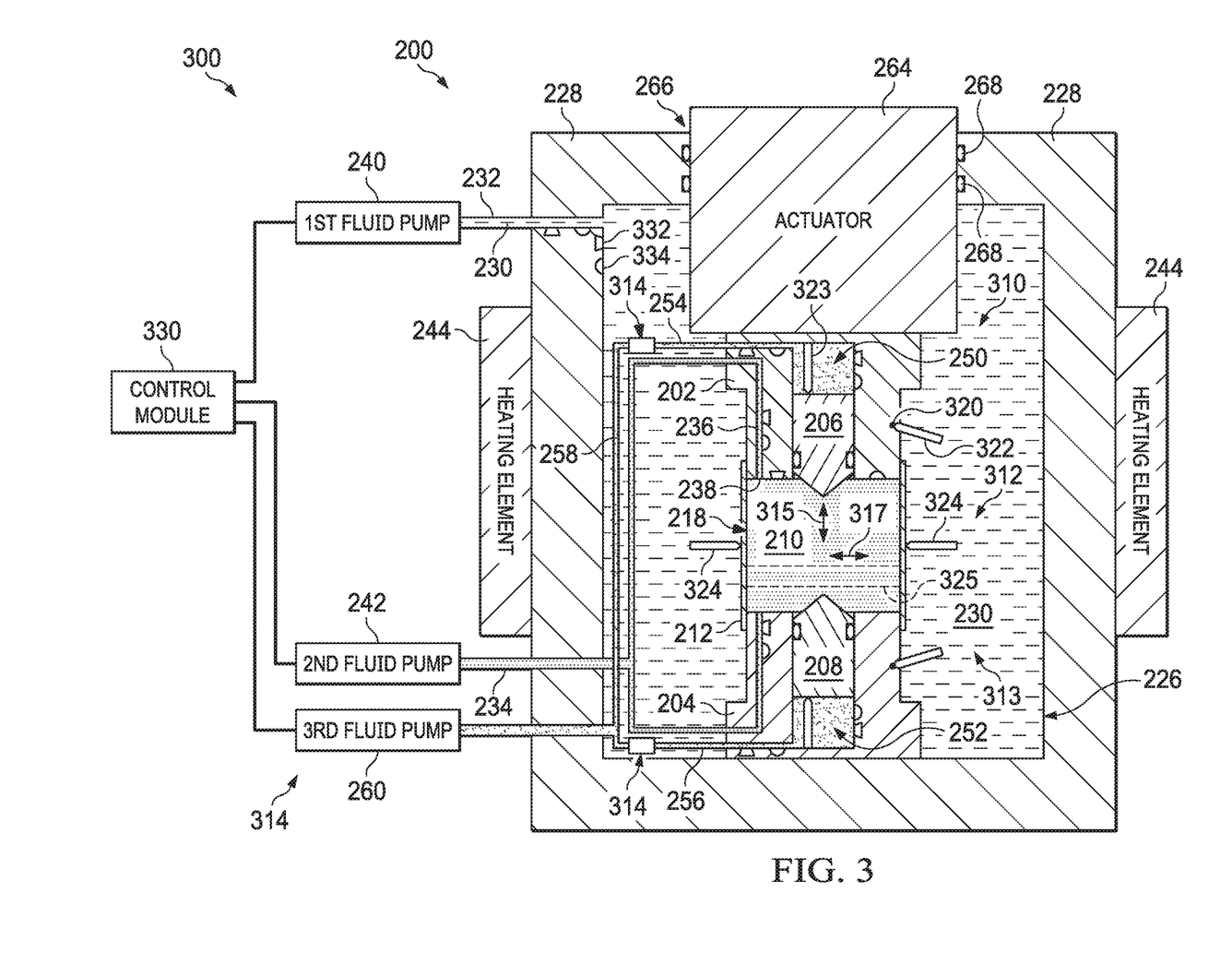
FIG. 3 schematically illustrates a view of an example system embodiment of the disclosure, the system including any of the apparatus embodiments discussed in the context of FIGS. 2A-2C.

Another embodiment of the disclosure is a system for measuring mechanical properties of a rock formation. FIG. 3 schematically illustrates a view of an example system 300 embodiment of the disclosure. Embodiments of the system 300 can comprise an apparatus 200 and one or more sensor devices 310, 312, 313, 314.

The apparatus 200 of the system 300 can include any of the components configured as discussed in the context of FIGS. 2A-2C, including: first and second fixtures 202, 204 each containing a force application fixture 206, 208, a confining sleeve 212, to form the specimen chamber 218, a confining chamber 226 having walls 228 to contain the first and second fixtures 202, 204, the confining sleeve 212 and the specimen 210 therein, and, to hold a hydraulic fluid 230 so as to exert a confining pressure on the confining sleeve 212; first channels 232 passing though the confining walls 228 that can add and remove the hydraulic fluid 230 to and from the confining chamber 226; second channels 234 passing though the confining walls 228 and one of the first and second fixtures 202, 204 that can add and remove a pore space fluid 236 to and from specimen chamber ports 238 open to the specimen chamber 218 to maintain a pore pressure equal to or less than the confining pressure while the stress is applied to the specimen.

In some embodiments of the apparatus 200 of the system 300, the first and second fixtures 202, 204 can include fixture chambers 250, 252 with the force application fixtures 206, 208 located therein and the fixture chambers 250, 252 connected to third channels 254, 256 configured to add or remove a second hydraulic fluid 258 to and from the fixture chambers 250, 252 and configured to hold the second hydraulic fluid 258 therein to apply a crushing pressure to the force application fixtures 206, 208, as discussed in the context of FIG. 2A. Some embodiments of the apparatus 200 of the system 300 include a mechanical force actuator 264 passing through at least one confining wall 228 to connect to the first or second fixture 202, 204 to apply the stress to the specimen as a tensile or compressive stress through the first or second fixture 202, 204, as discussed in the context of FIG. 2A.

The one or more sensor devices 310, 312, 313, 314, of the system 300 can be configured to measure displacement while the stress is applied the specimen 210 to facilitate quantifying the stress required to cause mechanical failure of the specimen 210.

For instance, in some embodiments, the sensors devices 310, 312, 313 can be or include linear variable differential transformer sensors configured to measure axial, lateral or circumferential displacements (e.g., in vertical direction 315 or horizontal direction 317, respectively, as shown in FIG. 3) of cylindrically-shaped specimens when the stress is applied as a compressive or tensile stress as part of compression or tensile strength testing.

For instance, in some embodiments, increasing amounts of the stress can be applied as a uniaxial compressive or tensile load (e.g., in direction 315 or 317) until breaking, buckling, deflection, displacement or other irreversible deformation of the specimen 210 occurs, as measured by the sensor devices 310, 312, 313.

For instance, in some embodiments, an axial displacement sensor 310 can include end pins 320 configured to be coupled to one or both of the first and second fixtures 202, 204 and connect to arms 322 of the axial displacement sensor 310, the arms 322 configured to record axial displacements (e.g., cantilevered arms configured measure changes in the distance between the first and second fixtures 202, 204) as the stress is applied to the specimen. In other embodiments, the sensor 310 can include arms 323 (e.g., a spring-loaded sensor arm) located in the fixture chambers 250, 252 and coupled to one or both of force application fixtures 206, 208 to record axial displacements (e.g., changes in the distance between the force application fixtures 206, 208) as the stress is applied to the specimen.

For instance, in some embodiments, a lateral displacement sensor 312 can similarly include arms 324 coupled to the outside surface of the confining sleeve 212 and configured to measure the lateral displacement of the specimen (e.g., changes in the distance between arms 324 located on opposite sides of the specimen) as the stress is applied to the specimen.

In some embodiments, a circumferential extensometer sensor 314 can include one or more strings or coils 325 wrapped around the circumference of the sleeve 212 and configured to measure changes in circumference (e.g., circumferential elongation) as the stress is applied to the specimen.

In still other embodiments, additionally or alternatively, the displacement of the force application fixtures 206, 208 can be determined by volume displacement measurements. That is, the volume of second hydraulic fluid 258 pumped into the fixture chambers 250, 252, to increase the crush pressure (Pcrsh) as part of applying the stress to the specimen, can be measured. By knowing the volume of hydraulic fluid pumped by the third pump 260 and knowing the volume of the chambers 250, 252, the axial displacement of the force application fixtures 206, 208 can be calculated (e.g., via the control module 330). Such volume displacement measurements have the advantage of not requiring sensors to measure linear or circumferential displacements. In some such embodiments, the third pump 260 can be configured to measure the volume pump, and as such, also serves as a volume displacement sensor 314. In other such embodiments, a separate volume sensor 314 (e.g., a flow meter coupled to one or both of the channels 254 256 configured to deliver the second hydraulic fluid 258) can be used to measure the volume of second hydraulic fluid 258 pumped into the fixture chambers 250, 252.

One skilled in the pertinent art would understand how axial, lateral, circumferential or volume displacements associated with the stress-induced failure of the specimen 210 could be recorded by the sensor devices 310, 312, 3.13, 314 in the form of voltages or other electrical signals, which are then transmitted (e.g., via wirelessly via RF transmissions or via wired data transmission lines) to a control module 330 (e.g., a computer or, application specific integrated circuit ASIC) configured for date recording and processing.

Embodiments of the system 300 can further include environmental sensors 332, 334 configured to measure the temperature and pressure conditions inside of the any one or all of the specimen chamber 218, the confining chamber 226, or fixture chambers 250, 252 and/or inside the respective channels 232, 234, 254, 256 connected to these chambers.

For instance, environmental sensors 332 configured as temperature gages can be located in or facing any of these chambers 218, 226, 250, 252 and/or in or facing the channels 232, 234, 254, 256 connected to these chambers to measure the temperature of the hydraulic fluid 230, pore space fluid 236 or second hydraulic fluid 258 inside of the respective chamber or channel that these fluids are located in. Such temperature data can be transmitted (e.g., wirelessly or via wired data transmission lines) to the control module 330 for data processing. Based upon such data, the control module 330 can send instructions (e.g., wirelessly or via wired data transmission lines) to the heating element 244 to increase or decrease applied heating as appropriate to maintain the specimen 210 at a desired target temperature during the application of the stress as part of the stress testing.

For instance, environmental sensors 334 configured as pressure gages can be located in or facing the environment of any of these chambers 218, 226, 250, 252 and/or in or facing the environment of any of the channels 232, 234, 254, 256 connected to these chambers to measure the pressure of the first hydraulic fluid 230, the pore space fluid 236 or the second hydraulic fluid 258 inside of the respective chambers or channels that these fluids are located in. Such pressure data can be transmitted (e.g., wirelessly or via wired data transmission lines) to the control module 330 for data processing. Based upon such data, the control module 330 can send instructions to the first or second pump 240, 242 (e.g., wirelessly or via wired data transmission lines) to increase or decrease pressure as appropriate to maintain the specimen 210 at a desired target pressure (e.g., Pconf and Ppore) during the application of the stress as part of the stress testing of a specimen 210. Based upon such data, the control module 330 can send instructions to the third pump 260 (e.g., wirelessly or via wired data transmission lines) to increase the crushing pressure (PCrsh) at a desired target rate as part of the stress testing of a specimen 210.

In some embodiments of the system 300, the control module 330 can be configured (e.g., programed) to calculate a tensile strength or a compression strength for the specimen 210, and combine these value with analogous values obtained from multiple measurements made on other specimens of the downhole material, the measurements conducted at different combinations of elevated temperature and/or pressure conditions simulative of the in situ down hole environment. The control module 330 can be configured to display the combined values as a 3-dimensional a mechanical failure envelop (e.g., a plot of the tensile strength or compression strength versus the temperature of the first hydraulic fluid 230 or pore space fluid 236 and versus the confining pressure (Pconf) or pore pressure (Ppore).

In some embodiments, any one or more of the sensors 310, 312 332, 334 can be integrated into and be part of the apparatus 200.

Another embodiment of the disclosure is a method of measuring mechanical properties of a downhole material. FIG. 4 presents a flow diagram of selected steps of an example method 400 of the disclosure. The method 400 can be implemented by any of the embodiments of the apparatus 200 and the system 300 such as discussed in the context of FIGS. 2A-3.

With continuing reference to FIGS. 1-3 throughout, embodiments of the method 400 can include a step 410 of placing a specimen 210 of the downhole material between force application fixtures 206, 208 of first and second fixtures 202, 204 of an apparatus 200. The method can include a step 415 of wrapping a confining sleeve 212 of the apparatus 200 around portions 214, 216 of the first and second fixtures 202, 204 that are nearest to the specimen 210 to form a sealed specimen chamber 218. The sealed specimen chamber dimensions are defined by an inner surface 220 of the confining sleeve 212 and ends 224, 224 of the first and second fixtures 202, 204 nearest the specimen 210. The method 400 can include a step 420 of placing the first and second fixtures 202, 204, confining sleeve 212 and specimen 210 inside a confining chamber 226 of the apparatus 200.

The order of steps 410, 415 and 420 could be carried out in various different sequences. For example, as part of step 410, of the specimen 210 can be placed on one force application fixtures (e.g., one of fixture 206, 208 coupled to one of fixtures 202, 204). Then as part of step 415, the confining sleeve 212 can be wrapped around the portion of the one fixture (e.g., one of portions 214, 216). Then as a continuation of steps 410 and 415 the other fixture (the other one of fixture 206, 208 coupled to the other of fixtures 202, 204), can be placed adjacent to the specimen 210 and the confining sleeve 212 can be wrapped around the portion of the other fixture (e.g., the other one of portions 214, 216). For example, as part of step 415, the confining sleeve 212 can be wrapped around the portion of the one fixture (e.g., one of portions 214, 216) and then as part of step 410 the specimen 210 can be placed on the one force application fixture. Then as a continuation of steps 410 and 415, the other fixture can be placed adjacent to the specimen 210 and the confining sleeve 212 can be wrapped around the portion of the other fixture. For example, as part of step 420, one of the force application fixtures (e.g., one of fixture 206, 208 coupled to one of fixtures 202, 204) can be placed inside the confining chamber 226, the specimen 210 can be placed on the one force application fixture and then the confining sleeve 212 can be wrapped around the portion of the one fixture while the fixture in the chamber 226. Then as part of step 410 the other one fixture (the other one of fixture 206, 208 coupled to the other one of fixtures 202, 204) can placed adjacent to the specimen after the specimen is in the chamber 226 and then as part of step 415 the confining sleeve 212 can be wrapped around the portion of the other fixture after the other fixture is placed in the chamber. Based on the present disclosure, one skilled in the pertinent art would appreciate how still different sequences of such steps could implied as part of the method 400.

The method 400 can include a step 425 of pumping a hydraulic fluid 230 into the confining chamber 226 to fill the confining chamber 230 with the hydraulic fluid 230 such that the hydraulic fluid 230 exerts a constant confining pressure (Pconf) on the confining sleeve 212 to maintain the seal of the sealed specimen chamber 218 and to maintain contact between the inner surface 220 of the confining sleeve 212 and the specimen 210. The method 400 can include a step 430 of pumping a pore space fluid 235 to fill the sealed specimen chamber 218 with the pore space fluid 235 including passing the pore space fluid 235 through one or more specimen chamber ports 238 open to the specimen chamber 218 such that the pore space fluid 235 maintains a constant pore pressure (Ppore) at the specimen chamber ports 238 that is equal to or less than the confining pressure (Pcore≤Pconf). The method 400 can include a step 435 of applying a stress (F) to the specimen 210 through the force application fixtures 206, 208, while maintaining the constant confining pressure to maintain contact between the inner surface 220 of the confining sleeve 212 and the specimen 210 and while maintaining the constant pore pressure, until mechanical failure of the specimen 210.

In some embodiments of the method 400, applying the stress (step 435) can include a step 440 of pumping a second hydraulic fluid 258 into fixture chambers 250, 252 of the first and second fixtures 202, 204. As disclosed in the context of FIG. 2A, at least a portion of each one of the force application fixtures 206, 208 can be located in one of the fixture chamber 250, 252 and third channels 254, 256 can be configured to add or remove the second hydraulic fluid 258 to and from one of the fixture chambers 250, 252. The fixture chambers 250, 252 can be configured to hold the second hydraulic fluid 258 therein such that the second hydraulic fluid 258 can apply a crushing pressure (Pcrsh) to the force application fixtures 206, 208 as part applying the stress. In some such embodiments, the applied crushing pressure is increased until the mechanical failure of the specimen (e.g., until mechanical compression failure).

In some embodiments of the method 400, applying the stress (step 435) can include a step 445 of applying a tensile stress or compressive stress by a mechanical force actuator 264. As disclosed in the context of FIG. 2A, the actuator 264 or actuators can be configured to pass through one or more openings 266 in one or more of the walls 228 of the confining chamber 226 to connect to one of the first or second fixtures 202, 204.

In some embodiments of the method 400, applying the stress (step 435) can include a step 450 of applying heat from a heating element 244 of the apparatus 200 to maintain the hydraulic fluid 230 at a constant temperature while the stress is applied to the specimen 210 in accordance with steps 440 or 445.

Some embodiments of the method 400 can include, as a starting step 455, providing a specimen of a downhole material.

For instance, providing the specimen in accordance with step 455 can include providing a core plug specimen the down hole rock formation material (e.g., one of formation intervals 108 or 110). One skilled in the pertinent art would be familiar with the operation of conventional coring tools, such as rotary coring tools, to obtain such a specimen. For instance, in some embodiments, providing the core plug specimen from the rock formation can include using downhole core drilling equipment to cut a cylindrically-shaped core plug specimen from axially diagonally or laterally oriented side wall portions of a well bore and catching and storage equipment to capture and transport the core plug sample to the surface to be placed between the force application fixtures 206, 208 in accordance with step 410.

For instance, providing the specimen in accordance with step 455 can include providing a cementitious specimen (e.g., cementitious material used to form a well bore casing 104, or, cement formed in fractures 112 from cementitious fracturing fluid). One skilled in the pertinent art would be familiar with how forming such a cementitious specimen can include mixing a dry cement binder material with water and other fracturing additives or proppants to form a cement slurry in a container (e.g., a cylindrically shaped contain) and then allowed to set under conditions analogous to that used to form a cement wellbore downhole annulus or cement fracturing material. After setting, the cylindrically shaped cement specimen can be removing from the container and placed between the force application fixtures 206, 208 in accordance with step 410.

Some embodiments of the method 400 can further include, after applying the stress until the mechanical failure of the specimen 210 (step 435): pumping the hydraulic fluid 230 out of the confining chamber 226 (step 460); pumping the pore space fluid 236 out of the specimen chamber 218

(step 465); removing the confining sleeve wrapped around the portions 214, 216 of the first and second fixtures 202, 204 (step 470); and, as a finish step, removing the mechanically failed specimen 210 from between the force application fixtures 206, 208 (step 475).

Based upon the present disclosure one skilled in the pertinent art would understand how the method 400 could be repeated for a plurality of different specimens of the down hole material but with the confining pressure and core pressure adjusted to a different value and/or repeating the method steps at different temperatures in order to obtain sufficient information to produce a mechanical failure envelop to determine at what stresses under the simulated down hole environmental conditions the specimen would fail.

Those skilled in the art to which this application relates will appreciate that other and further additions, deletions, substitutions and modifications may be made to the described embodiments.

What is claimed is:

1. An apparatus for measuring mechanical properties of a downhole material, the apparatus comprising:
first and second fixtures each containing a force application fixture, the force application fixture configured to apply a stress to a specimen of the downhole material when located in-between the first and second fixtures;
a confining sleeve configured to wrap around portions of the first and second fixtures that are nearest to the specimen to form a sealed specimen chamber, the sealed specimen chamber dimensions defined by an inner surface of the confining sleeve and ends of the first and second fixtures nearest the specimen;
a confining chamber having walls configured to contain the first and second fixtures, the confining sleeve and the specimen therein, wherein the confining chamber is configured to hold a hydraulic fluid therein such that the hydraulic fluid can exert a confining pressure on the confining sleeve to maintain the seal of the sealed specimen chamber and to maintain contact between the inner surface of the confining sleeve and the specimen when the stress is applied to the specimen;
one or more first channels passing though one or more of the walls of the confining chamber, the one or more first channels configured to add and remove the hydraulic fluid to and from the confining chamber; and
one or more second channels passing though one or more of the walls of the confining chamber and through one of the first and second fixtures, the one or more second channels configured to add and remove a pore space fluid to and from specimen chamber ports open to the specimen chamber, wherein the pore space fluid is configured to maintain a pore pressure at the specimen chamber ports that is equal to or less than the confining pressure while the stress is applied to the specimen.

2. The apparatus of claim 1, wherein:
the first channels are connected to a first pump, the first pump configured to maintain the confining pressure constant while the stress is applied to the specimen, and,
the second channels are connected to a second pump, the second pump configured to maintain the pore pressure constant while the stress is applied to the specimen.

3. The apparatus of claim 1, further including a heating element configured to maintain the hydraulic fluid at a constant temperature while the stress is applied to the specimen.

4. The apparatus of claim 1, wherein an end of each of the force application fixtures nearest the specimen includes wedge-shaped or protruding point-shaped crush fixtures.

5. The apparatus of claim 1, wherein the first and second fixtures each include a fixture chamber, wherein:
at least a portion of each one of the force application fixtures is located in the respective fixture chamber of the first or second fixture;
each of the fixture chambers is connected to one or more third channels configured to add or remove a second hydraulic fluid to and from the one fixture chamber; and
the fixture chambers are configured to hold the second hydraulic fluid therein such that the second hydraulic fluid can apply a crushing pressure to the force application fixtures as part of applying at least a portion of the stress as a compressive stress or a tensile stress to the specimen.

6. The apparatus of claim 5, wherein:
each of the one or more third channels pass through one or more of the walls of the confining chamber and though one of the first and second fixtures to the respective fixture chamber; and
the one or more third channels are connected to a third pump, the third pump configured to apply adjustable amounts of the crushing pressure as part of applying the compressive stress to the specimen until compression failure of the specimen.

7. The apparatus of claim 5, wherein the first and second fixtures further include one or more gaskets located between the fixture chamber and the force application fixture in the fixture chamber, the one or more gaskets configured to prevent an exchange between the second hydraulic fluid in the fixture chamber and the pore space fluid in the specimen chamber.

8. The apparatus of claim 1, further including a mechanical force actuator, the actuator configured to pass through one or more openings in one or more of the walls of the confining chamber to connect to one of the first fixture or the second fixture, the actuator configured to apply at least a portion of the stress through the one first fixture or second fixture to the specimen as a compressive stress or a tensile stress until mechanical failure of the specimen.

9. The apparatus of claim 8, further including one or more second gaskets located between the one or more openings in the confining walls and the actuator, the one or more second gaskets configured to prevent an escape of the hydraulic fluid from the confining chamber.

10. The apparatus of claim 1, wherein the specimen of the downhole material can include: a cementitious or resin material for use to form a wellbore downhole annulus, cementitious or resin material for use as a fracturing fluid, or, a core plug of a downhole rock formation.

11. The apparatus of claim 1, wherein the hydraulic fluid includes hydraulic oil, the pore space fluid includes: formation fluid, completion fluid, gas, water, or brine, and, the second hydraulic fluid includes another hydraulic oil.

12. A system for measuring mechanical properties of a rock formation, the system comprising:
an apparatus including:
first and second fixtures each containing a force application fixture, the force application fixture configured to apply a stress to a specimen of the downhole material when located in-between the first and second fixtures;
a confining sleeve configured to wrap around portions of the first and second fixtures that are nearest to the specimen to form a sealed specimen chamber, the sealed specimen chamber dimensions defined by an inner surface of the confining sleeve and ends of the first and second fixtures nearest the specimen;

a confining chamber having walls configured to contain the first and second fixtures, the confining sleeve and the specimen therein, wherein the confining chamber is configured to hold a hydraulic fluid therein such that the hydraulic fluid can exert a confining pressure on the confining sleeve to maintain the seal of the sealed specimen chamber and to maintain contact between the inner surface of the confining sleeve and the specimen when the stress is applied to the specimen;

one or more first channels passing though one or more of the walls of the confining chamber, the one or more first channels configured to add and remove the hydraulic fluid to and from the confining chamber;

one or more second channels passing though one or more of the walls of the confining chamber and through one of the first and second fixtures, the one or more second channels configured to add and remove a pore space fluid to and from specimen chamber ports open to the specimen chamber, wherein the pore space fluid is configured to maintain a pore pressure at the specimen chamber ports that is equal to or less than the confining pressure while the stress is applied to the specimen; and a sensor device configured to measure a displacement of the specimen while the stress is applied to the specimen.

13. The system of claim 12, wherein the first and second fixtures each include a fixture chamber, wherein:

at least a portion of each one of the force application fixtures is located in the respective fixture chamber of the first or second fixture;

each of the fixture chambers is connected to one or more third channels configured to add or remove a second hydraulic fluid to and from the one fixture chamber; and the fixture chambers are configured to hold the second hydraulic fluid therein such that the second hydraulic fluid can apply a crushing pressure to the force application fixtures as part of applying at least a portion of the stress applied to the specimen.

14. The system of claim 12, further including a mechanical force actuator, the actuator configured to pass through one or more openings in one or more of the walls to connect to one of the first fixture or the second fixture, the actuator configured to apply at least a portion of the stress as a tensile or compressive stress through the one first fixture or the one second fixture to the specimen.

15. A method of measuring mechanical properties of a downhole material, comprising:

placing a specimen of the downhole material between force application fixtures of first and second fixtures of an apparatus;

wrapping a confining sleeve of the apparatus around portions of the first and second fixtures that are nearest to the specimen to form a sealed specimen chamber, the sealed specimen chamber dimensions defined by an inner surface of the confining sleeve and ends of the first and second fixtures nearest the specimen;

placing the first and second fixtures, the confining sleeve and the specimen inside a confining chamber of the apparatus;

pumping a hydraulic fluid into the confining chamber to fill the confining chamber with the hydraulic fluid such that the hydraulic fluid exerts a constant confining pressure on the confining sleeve to maintain the seal of the sealed specimen chamber and to maintain contact between the inner surface of the confining sleeve and the specimen;

pumping a pore space fluid to fill the sealed specimen chamber with the pore space fluid including passing the pore space fluid through one or more specimen chamber ports open to the specimen chamber such that the pore space fluid maintains a constant pore pressure at the specimen chamber ports that is equal to or less than the confining pressure; and applying a stress to the specimen through the force application fixtures, while maintaining the constant confining pressure to maintain contact between the inner surface of the confining sleeve and the specimen and while maintaining the constant pore pressure, until mechanical failure of the specimen.

16. The method of claim 15, wherein applying the stress includes pumping a second hydraulic fluid into fixture chambers of the first and second fixtures, wherein:

at least a portion of each one of the force application fixtures is located in the respective fixture chamber of the first or second fixture;

each of the fixture chambers is connected to one or more third channels configured to add or remove the second hydraulic fluid to and from the one fixture chamber; and the fixture chambers are configured to hold the second hydraulic fluid therein such that the second hydraulic fluid can apply a crushing pressure to the force application fixtures as part of applying the stress.

17. The method of claim 16, wherein the applied crushing pressure is increased until the mechanical failure of the specimen.

18. The method of claim 15, wherein applying the stress includes applying a tensile or compressive stress by a mechanical force actuator, the actuator configured to pass through one or more openings in one or more of the walls of the confining chamber to connect to one of the first fixture or the second fixture.

19. The method of claim 15, wherein applying the stress includes applying heat from a heating element of the apparatus to maintain the hydraulic fluid at a constant temperature while the stress is applied to the specimen.

20. The method of claim 15, further including, after the applying of the stress until the mechanical failure of the specimen:

pumping the hydraulic fluid out of the confining chamber;

pumping the pore space fluid out of the specimen chamber;

removing the confining sleeve wrapped around the portions of the first and second fixtures; and removing the mechanically failed specimen from between the force application fixtures.

* * * * *